Figure 1:
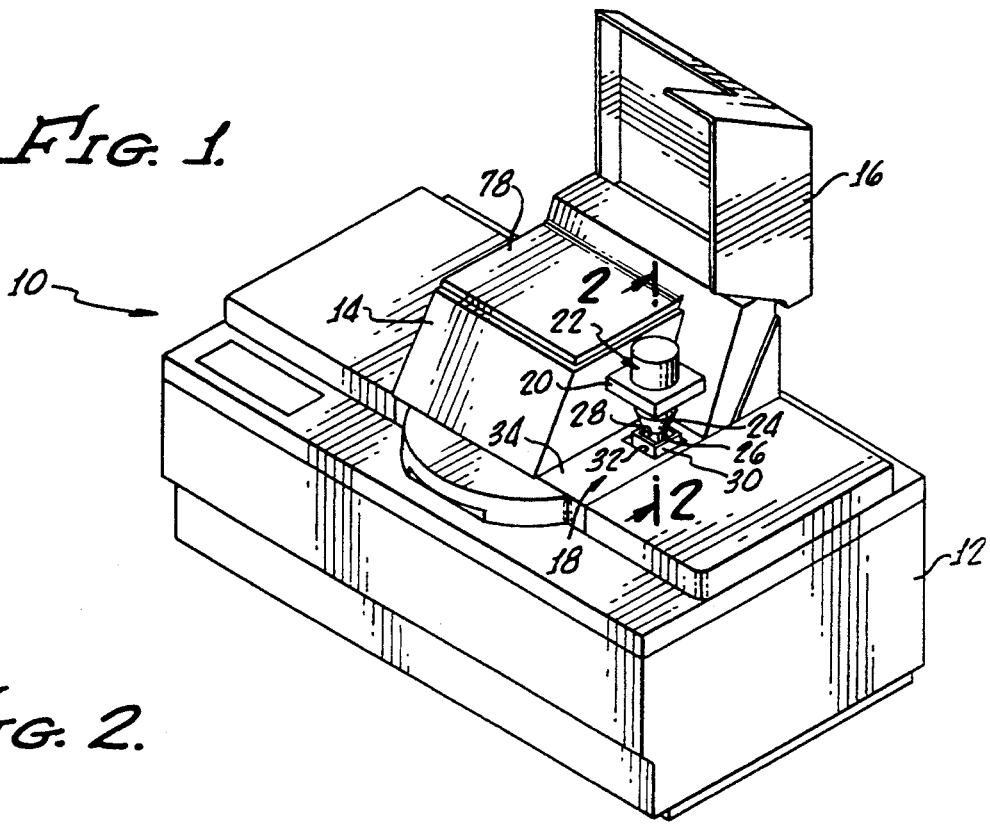

United States Patent [19]

Mott et al.

[11] Patent Number: 5,341,963

[45] Date of Patent: Aug. 30, 1994

[54] APPARATUS FOR DISPENSING DRY PARTICLES

[75] Inventors: Steven C. Mott; Craig A. Wright, both of San Diego, Calif.

[73] Assignee: Horiba Instruments, Inc., Irvine, Calif.

[21] Appl. No.: 9,887

[22] Filed: Jan. 27, 1993

[51] Int. Cl.$^5$ .................................................. B67D 5/64
[52] U.S. Cl. ................................ 222/287; 222/161; 222/196; 222/282; 222/522; 222/457
[58] Field of Search ............... 222/160, 161, 196, 199, 222/200, 457, 282, 287, 181, 185, 522, 559, 548, 549

[56] References Cited

U.S. PATENT DOCUMENTS

| | | | |
|---|---|---|---|
| H257 | 4/1987 | Barditch et al. | 239/124 |
| 1,794,023 | 2/1931 | Liberthal | 222/522 X |
| 3,193,153 | 7/1965 | Hosokawa | 222/199 |
| 3,278,090 | 10/1966 | Wahl | 222/199 |
| 3,618,828 | 11/1971 | Schinella | 222/457 X |
| 3,934,762 | 1/1976 | Urayama | 222/200 |
| 3,938,259 | 2/1976 | Ormos et al. | 34/10 |
| 3,939,714 | 2/1976 | Miller, Jr. | 73/424 |
| 3,990,857 | 11/1976 | Vandenhoeck | 222/457 X |
| 4,047,814 | 8/1977 | Westcott | 356/38 |
| 4,070,765 | 1/1978 | Hovmand et al. | 34/10 |
| 4,213,325 | 7/1980 | Tumanov et al. | 73/1 G |
| 4,298,168 | 11/1981 | Rozmus | 222/161 X |
| 4,359,175 | 11/1982 | Lizenby | 222/199 |
| 4,450,983 | 5/1984 | Goodrich | 222/200 X |
| 4,515,274 | 5/1985 | Hollinger et al. | 209/3.1 |

FOREIGN PATENT DOCUMENTS 907131 10/1962 United Kingdom ............... 222/199

Primary Examiner—Kevin P. Shaver
Attorney, Agent, or Firm—Poms, Smith, Lande & Rose

[57] ABSTRACT

A particle analyzer includes a vibratory driver for particulate samples which are received in a sample cup to be drizzled under controller vibration to an analysis cell of the analyzer along with a conveying air stream. The driver is arranged to impose orbital oscillatory motion in a vertical plane on the sample cup to roll the sample while assisting in sifting of the sample through conventional sieve screen sample cups. Avoidance of vibratory classification of the sample by particle size while the test is in progress, as well as avoidance of sample compaction is achieved with the described driver. Additionally, an improved predictability of sample feed rate control results from the use of the orbital driver also with a novel sample cup not utilizing a sieve screen, but employing the inherent characteristic of particulate materials to form an repose angle when piled up. The novel sample cup provides a ledge surface upon which particulates are piled in their inherent angle of repose preparatory to being vibrationally dislodged and drizzled over an edge of the ledge. The repose angle of the particulates is continuously refilled from a bulk sample of the particulates as particles are drizzled to the analyzer. Structure is provided for adapting the sample cup to a variety of particulates, regardless of whether they be free-flowing or somewhat cohesive.

10 Claims, 3 Drawing Sheets

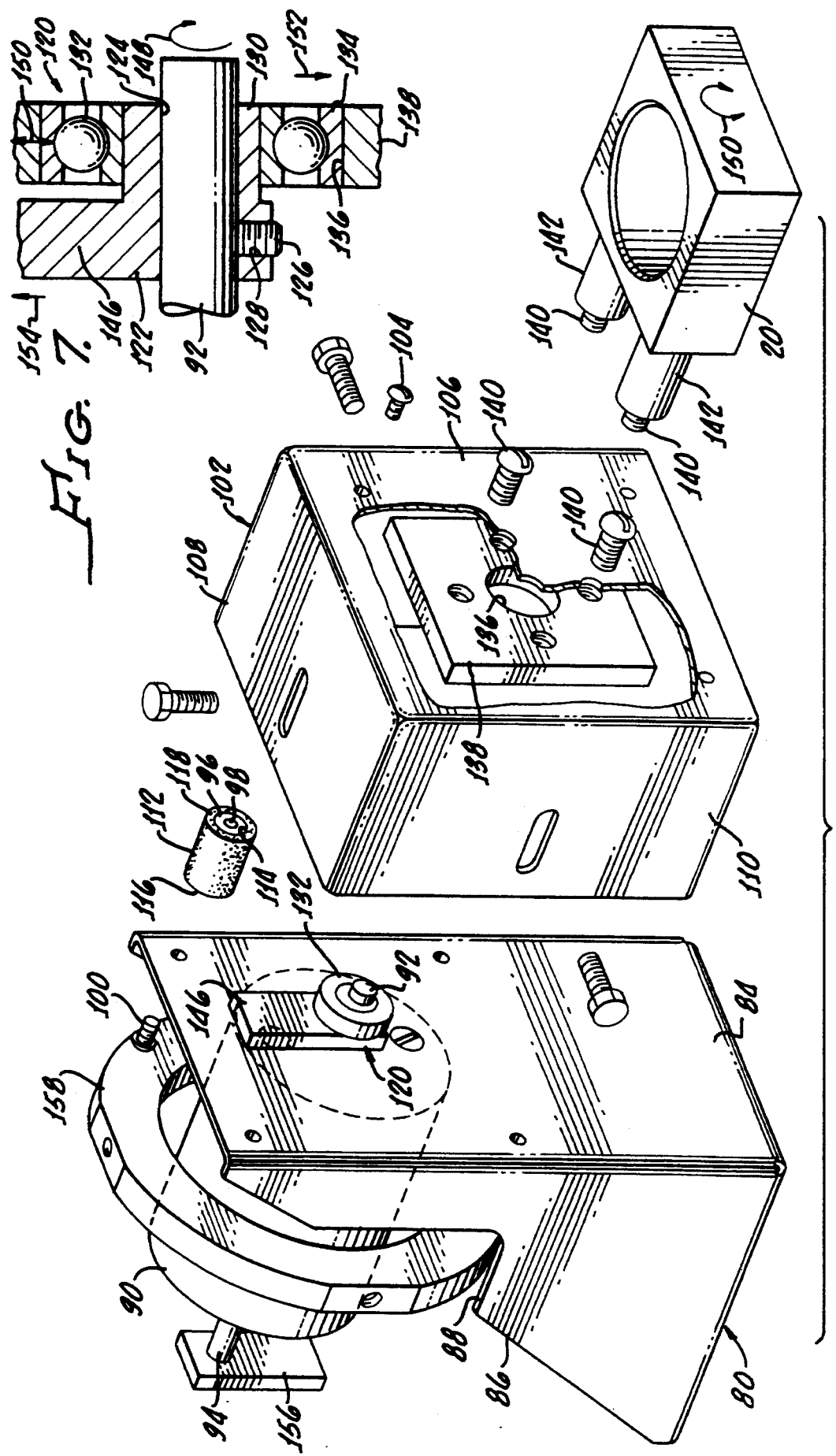

APPARATUS FOR DISPENSING DRY PARTICLES

BACKGROUND OF THE INVENTION

1. Field of the Invention

The present invention relates to a feeder apparatus and method for dispensing particulates. More particularly, the present invention relates to apparatus and methods for controllably drizzling both free-flowing dry particles and particles which may not be entirely dry nor truly free-flowing (i.e., particles which may be somewhat moist, sticky, tacky, or cohesive so that they may tend to aggregate or clump) from a bulk sample of the particles into an air stream conveying the particles through an analysis cell of a particle analyzer. In the analysis cell, optical methods including light back scatter, forward scatter or diffraction, and obscuration effects are employed to interrogate the particles for certain physical characteristics, such as particle size distribution of the bulk sample.

2. Related Technology

Present dry particle analyzers generally use two methods to feed particulate materials from a bulk sample of the material into a conveying air stream. For materials which are not too free flowing (i.e., are moist, tacky, or tend to aggregate), the feeder includes an auger metering particles from a container for the bulk sample into a vibratory trough. The vibratory trough employs a downward incline in addition to a selectively variable level of imposed vibration to deliver the particles to an end of the trough which is suspended over the mouth of an air intake duct. When the particles drop from the trough end, a vacuum system draws the particles and a conveying ambient air stream into the air intake. Apparently, the thinking behind this type of feeder is that the vibration of the duct will break up any agglomerations of the particles, and that a technician can control the turning rate of the auger and vibration rate of the trough to produce a desired rate of particle feed from the bulk sample.

Experience with the auger and trough feeder has shown, however, that if the particles tend to form agglomerations, they arrive at the end of the trough pretty much like they entered it. That is, with some materials the agglomerations are not in fact broken up by the vibrations of the trough, and the material enters the analyzer in clumps and bunches rather than as a steady drizzle. Of course, this inconsistent delivery of the particles to the analysis cell detrimentally affects the accuracy of testing.

An important aspect of this type of particle testing is control of the obscuration effect of the particles in the analysis cell. That is, control of the extent to which the flow of particles in the air stream blocks light from passing through the cell is fundamental to this type of particle testing. An inconsistent flow of particulates to the cell makes it virtually impossible to accurately control the light obscuration and adversely affects the test accuracy. Additionally, to the extent that the skill of the technician influences the sample feeding rate, and the resulting accuracy of the particle test, test accuracy and repeatability of particle analysis tests conducted with this type of sample feeding might be in question.

Another type of particle feeder primarily for particles which are truly dry and free-flowing includes a sample cup having an upper chamber floored with a sieve screen. Below the sieve screen, the sample cup includes a funnel-like portion with a spout leading to the mouth of the air intake duct. When the sample cup is vibrated or oscillated, the particles sift through the sieve screen and drizzle out of the spout of the funnel-like portion to be conveyed by the air stream to the analysis cell of the particle analyzer.

Unfortunately, the conventional sieve cup tends to classify some particle samples even as the sample is being fed into the particle analyzer. That is, the sieve screen needs to be fine enough to hold back the bulk sample while no vibration or oscillation is being applied to the sample cup. In other words, the sieve screen can not be so coarse that the bulk particulate sample simply flows through like a liquid. In fact, the sieve screen needs to be additionally fine enough to also hold the fines of the sample as part of the bulk while not agitated. The lower portion of the sample immediately above the sieve screen would otherwise be partially depleted of these fines before the test could begin. On the other hand, the sieve screen can not be so fine a mesh that the coarse particles of the sample will not sift through even under agitation.

Regardless of the mesh size of sieve screen selected, while a bulk sample is being drizzled with controlled vibration to a particle analyzer, the fines of the sample may tend to migrate downwardly through the coarse particulates, and to pass freely through the sieve screen. At the same time, the coarser particulates may tend to be held back at the sieve screen and to sift through less readily. As a result, when vibration is initially applied to the sample cup to begin drizzling the sample to the analyzer, the initial portion of the bulk sample drizzled to the analyzer may be representative of the bulk. However, an interval may then follow during which a second part of the sample which is rich in fines is drizzled to the analyzer. As these fines migrate to the sieve screen through the bulk of the sample they pass immediately through the sieve screen ahead of coarser particulates and leave a remainder of the bulk sample which is depleted of fines. Finally, the remainder of the sample, rich in coarse particulates and depleted of fines is drizzled to the analyzer. The result is a time-variant classification of the bulk sample which may result in a decreased accuracy of measurement of the particle size distribution of the sample. Thus, a design paradox is presented to those who would use a simple sieve screen to feed a drizzle of particles to a particle analysis cell. No matter the sieve mesh chosen, a detrimental effect may be encountered with some particulate materials.

Additionally to the above, regardless of whether a conventional sieve screen sample cup or the Applicants' new type of sample cup as described herein is used to drizzle particulates, the Applicants have discovered that the nature of the applied vibrations has a considerable effect on the feeding of the particles. That vibration in a horizontal plane, whether purely linear reciprocation, tapping, Jiggling, orbital, or other motion, simply rolls the particles around on the upper side of the sieve screen, and provides no driving force to assist the particles through the sieve, beyond that already present from gravity. On the other hand, if a vertical shaking or reciprocation is applied to the particles, this motion simply tends to tamp or pack down some materials into a plug which will not thereafter drizzle as desired. This tamping or packing effect of purely vertical dispensing motion seems to affect all sample cup designs. Such is especially the case with materials like corn starch which tend to clump. Also, the rate of feeding of particles out of the bulk sample and into the particle analyzer may not be proportionate with the vibration rate. In some cases with some materials, the rate of particle feed may actually decrease with an increased vibration rate. Such an inverse feed rate relationship makes control of test conditions very difficult.

SUMMARY OF THE INVENTION

In view of the above, the present invention provides an apparatus and method for dispersing free-flowing dry particles in which a sample cup includes a sample chamber communicating with a downwardly-extending spout closed at its lower end by a floor. Above the floor, at least one window having an upper and a lower edge opens outwardly of the sample cup chamber to a ledge extending horizontally outwardly of the window and ending at a vertical drop-off edge. Structure is provided for selectively moving and retaining the ledge relative the window edges so that free-flowing and other particles may repose on the ledge. In the absence of vibration, the particles simply lay on the ledge with an angle of repose characteristic of the particulate bulk. This repose angle extends the particles downwardly and outwardly from the upper edge of the window toward the drop-off edge. Thus, dependent upon the vertical position of the ledge relative to the upper window edge, the repose angle of the particulates will extend from the window only partway or almost all the way across the ledge toward the drop-off edge. So long as the repose angle stops short of the drop-off edge, particles will not freely flow out of the sample cup.

When vibration is applied to the sample cup, particles drizzle over the drop-off edge of the ledge and into the particle analyzer along with a conveying air stream. As particles drop from the ledge, additional particles flow out the window to fill out the angle of repose of the particulates. Dependent on how far below the top window edge the ledge is positioned, all or only a part of the window may be available for particle flow, and the particles may repose all or only part of the way across the ledge toward the drop-off edge. Thus, the rate at which particles are discharged from the sample cup in response to vibration is easily and repeatably adjusted.

The present invention also provides a sample cup vibratory driver in which an orbital oscillatory motion in a vertical plane, and substantially without angular rocking, is imposed upon the sample cup. This vertical orbital motion tends to toil the entire bulk sample in the sample cup so that homogeneity of the sample is maintained. Also, the vertical aspect of the orbital motion provides an acceleration in addition to gravity to assist the particles through the sieve screen when such a sample cup is used with the vibratory driver. The rate of orbiting may by increased to the level desired for urging the particles through the sieve. On the other hand, the vertical orbital motion seems to prevent the undesirable packing of the sample which sometimes results from the purely vertical shaking or reciprocation discussed above.

By avoidance of angular rocking is meant the maintenance of the sample cup in a vertical orientation during its orbital motion. Because the intake to the particle analyzer is generally not much bigger than the outlet of the sample cup, avoidance of angular rocking is thought to be desirable both to avoid having particles flung outside of the intake, and to avoid collision of the sample cup with the analyzer intake. Desirably, the diameter of the vertical orbit of the sample cup may be kept small enough to allow the spout of the sample cup to be received into the analyzer intake. Thus, lose of particulates outside the analyzer intake is avoided.

While the above-described vibratory sample cup driver is advantageously useable with conventional sieve screen sample cups, the Applicants have determined that the combination of the vertical orbital vibratory motion for the sample cup along with the above-described, "window ledge" type of sample cup, results in reduced classification of the sample by size, a resulting increase in uniformity of feeding of the bulk sample to a particle analyzer, and an important monotonic relationship between oscillation rate and sample feed rate. That is, an increase or decrease in the rate of vibration applied to the sample cup results in a respective increase or decrease in the rate of particle drizzle to the test cell. While the monotonic relationship may not necessarily be linear, at no time should the vibration rate and particle feed rate display an inverse relationship, as can sometimes be the case with conventional sieve screen sample cups and vibrators. A technician using the combination of the "window ledge", sample cup with the vertical orbital vibratory cup driver provided by the present invention will be able to much better control the rate and consistency of drizzling of a sample to the test cell of a particle analyzer. Thus, the accuracy and repeatability of particle size distribution tests conducted with the invention is considerably improved over the prior technology.

Further, the vibratory driver provided by the present invention is very low in both audible and structural noise. Consequently, the vibratory drive and sample cup may be associated directly with the rest of the particle analyzer without impairing the delicate optical system of the analyzer. In fact, the vibratory drive may be stacked on the particle analyzer above the analysis cell thereof with a resulting vast improvement in particle flow for the analyzer, and decrease in space needed for the apparatus.

The above, and other advantages of the present invention will be appreciated from a reading of the following detailed description of a single preferred embodiment of the invention taken in conjunction with the following drawing Figures, in which:

BRIEF DESCRIPTION OF THE DRAWINGS

FIG. 1 provides a perspective view of an exemplary particle analyzer embodying the invention;

FIG. 2 is an enlarged fragmentary view of a portion of FIG. 1, with parts omitted for clarity of illustration;

FIG. 3 provides a further enlarged fragmentary view of a portion of FIG. 2;

FIG. 4 is a side elevation view of a portion of the apparatus shown in FIG. 1, with a protective cosmetic cover broken away and partially in cross section to better illustrate the depicted structure;

FIG. 5 provides a plan view of the structure shown in FIG. 4;

FIG. 6 is an exploded view of the structure shown in the preceding Figures, with parts thereof omitted or broken away to better illustrate the structure; and FIG. 7 provides an enlarged fragmentary view of a portion of the structure also shown in FIG. 6.

DETAILED DESCRIPTION OF THE PREFERRED EMBODIMENT

Viewing FIG. 1, a particle analyzer 10 includes a housing 12 which may sit upon a bench top (not shown). The particle analyzer 10 includes a dry particle feeder 14 which is stacked upon the remainder of the analyzer 10, and includes a cover portion 16, shown in an open position. The open cover 16 reveals a sample chamber 18 at the right-hand side of the dry particle feeder 14 wherein is disposed a vibratory cap clamp 20 holding a sample cup 22. Sample cup 22 includes a funnel-like lower portion 24 with a spout 26 extending downwardly into the open upper end or mouth 28 of a conduit member 30. The conduit member 30 extends upwardly through an opening 32 defined by a cover plate portion 34 of the dry particle feeder 14. Cover plate 34 spans across a well (not seen in FIG. 1, but referenced with numeral 36 in FIG. 2), wherein is disposed a dry particle analysis cell, which is not further detailed, but which may be used to interrogate the particles drizzled therethrough in a conveying air stream.

Figure 2:
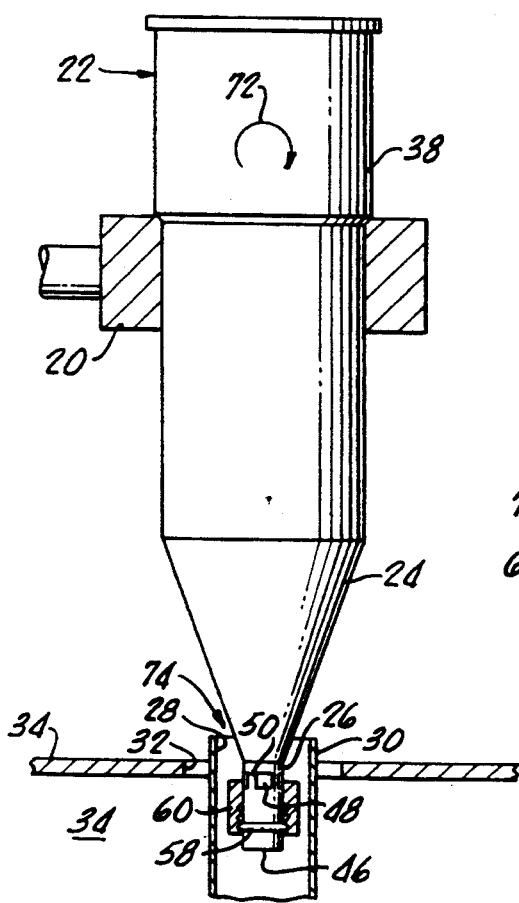
Figure 3:
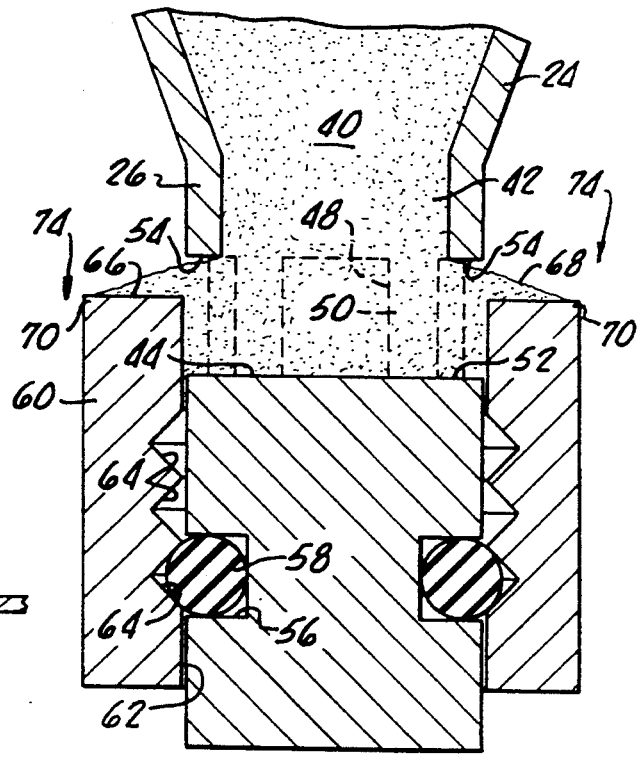

Turning to FIGS. 2 and 3 for a more detailed view of the exemplary embodiment of the invention, it is seen that the sample cup 22 includes an upwardly open cylindrical portion 38 defining a sample chamber 40 into which a powdered, granular, or otherwise particulate sample 42, viewing FIG. 3, may be placed for particle size analysis using the analyzer 10. The sample chamber 40 communicates downwardly in the funnel-like lower portion 24 of the sample cup 22, and into the spout 26 thereof. A floor portion 44 of the spout 26 closes the lower end of the sample chamber 40. Below the floor portion 44, the spout 26 extends downwardly an additional short distance to terminate at a lower end 46. Immediately above the floor 44, four windows 48, which are separated by four ribs 50, are defined by the sample cup 22, viewing particularly FIG. 3. The windows 48 include a lower edge 52 at the level of floor 44, and an upper edge 54 spaced above lower edge 52 and floor 44. While the exemplary embodiment of the invention depicted by the drawing Figs. includes four windows 48 which are separated by four ribs 50, other numbers of windows and ribs could also be employed. For example, if a particulate material including clumps is to be drizzled to an analyzer 10, a larger number of windows each of which is small enough to prevent passage of the clumps may be preferred. Such a configuration of sample cup would possibly allow the vibration imposed on the sample cup to break up the clumps without ever allowing excessively large clumps to fall to the analyzer 10. On the other hand, a lower number of windows which may also be smaller in comparison to the size of the ribs may be preferred. This configuration of feed cup might be useful, for example, to very slowly drizzle freely flowing particulates to a particle analyzer.

Between the level of the floor 44, and lower end 46, the sample cup 22 includes a circumferential groove 56 which in the depicted exemplary embodiment of the invention receives an O-ring type resilient member 58, still viewing FIG. 3. Movably retained on the spout 26 by the resilient member 58, is a collar member 60. This collar member 60 defines a bore 62 closely receiving the spout 26, and on the bore 62 also defines three grooves 64, by which the resilient member 58 retains the collar member 60 in a selected one of three vertical positions along the spout 26. At its upper extent, the collar member 60 defines a ledge surface 66 which is horizontal, and which is disposed outwardly of the windows 48.

Those ordinarily skilled in the pertinent arts will recognize that the O-ring member 58 yieldably snaps into any one of the three grooves 64 to form a supporting detent for the collar member 60. However, a variety of alternative supportive detent structures may be employed to locate and retain the collar member on spout portion 26. For example, a spring-loaded detent ball may be carried by the spout portion 26 below the level of the floor portion 44 and above the lower end 46 thereof. Such a spring loaded detent ball would be laterally movable relative to the spout portion 26, and would be receivable into the grooves 64 to retain the collar portion 60 in a selected position relative to the windows 48.

In its position depicted in FIG. 3, the collar member 60 obstructs about three-fourths of the vertical opening of the windows 48. That is, the ledge surface 66 is disposed below the top edge 54 of the windows 48 by about one-fourth of the vertical height of the windows. Below the ledge surface 66, the collar member 60 prevents flow of particles from sample 42 outwardly through the windows 48. Above the ledge surface 66, the particles flow outwardly onto the ledge surface, and define a cone-like angle of repose 68, particularly viewing FIG. 3. The angle at which particles will repose on the ledge 66 or elsewhere is a characteristic of the particles themselves, and as depicted for the sample 42, stops just short of the outer edge 70 of the ledge surface 66. The depicted position for the collar member 60 would be used for particulates which flow very easily, or which must be drizzled to the analyzer 10 at a comparatively slow rate. That is, this depicted position for the collar member 60 would be expected to be used with particulate materials which do not inherently aggregate, clamp, or cohere, but which are dry, and free-flowing. Dependent upon the nature of the particles to be drizzled with the sample cup 22, the collar member 60 is easily snapped to any one of the three positions made possible by the three grooves 64. So long as the angle of repose of the particular sample stops short of the edge 70 of the ledge surface 66, the sample will be retained in the sample chamber 40 and will not flow freely therefrom without agitation.

The lowermost position for the collar 60 places the ledge surface 66 at the level of the floor 44, and would be used with materials which do not flow too well. On the other hand, an intermediate or middle position for the collar member 60 increases by a factor of about two the height of the window 48 which is available for particle flow, in comparison to that shown in FIG. 3.

In addition to a close fit of the collar member 60 about the spout 26, which resists passage of particle downwardly in the bore 62 between the outside of spout 26 and the inside of collar 60, the engagement of the O-ring member 58 with both the spout 26 and collar 60 acts as a seal to positively prevent such uncontrolled loss of the particles. Thus, the sample cup 22 may be adjusted to any one of three, or additional, configurations as desired to adapt the sample cup to drizzle particulates to the analyzer 10 at a desired rate, as is to be further explained below.

When vibration is imposed on the sample cup 22 (as depicted by arrow 72), particles are dislodged from the angle of repose 68 on the ledge surface 66, and tumble over the edge 70 into the intake of conduit 30 along with a conveying air stream (arrows 74). As particles are dislodged from the repose angle 68, additional particles flow outwardly from chamber 40 via the open part of the windows 48, and onto the ledge 66. In this way, an easily controlled and consistent drizzle of particles from the sample 42 into the particle analyzer 10 is achieved.

In order to orbitally oscillate the sample cup 22 in a vertical plane, as discussed above, a vibratory driver 76 is provided. The vibratory driver 76 is disposed on the left-hand side of the particle feeder 14 under a cover 78, carries the clamp 20 for receiving the sample cup 22, and is more fully depicted in FIG. 4. With particular attention now to FIGS. 4–7 in conjunction, it is seen that the driver 76 includes a motor bracket 80 which is carried on a base plate 82 of the particle feeder 14. Motor bracket 80 includes a vertical front plate portion 84, and a pair of side plate portions 86, the latter defining notches at 88 for a purpose to be identified below. The motor bracket 80 carries a variable-speed, double end shaft motor 90, the opposite end shaft portions of which are referenced with the numerals 92, and 94.

Figure 5:
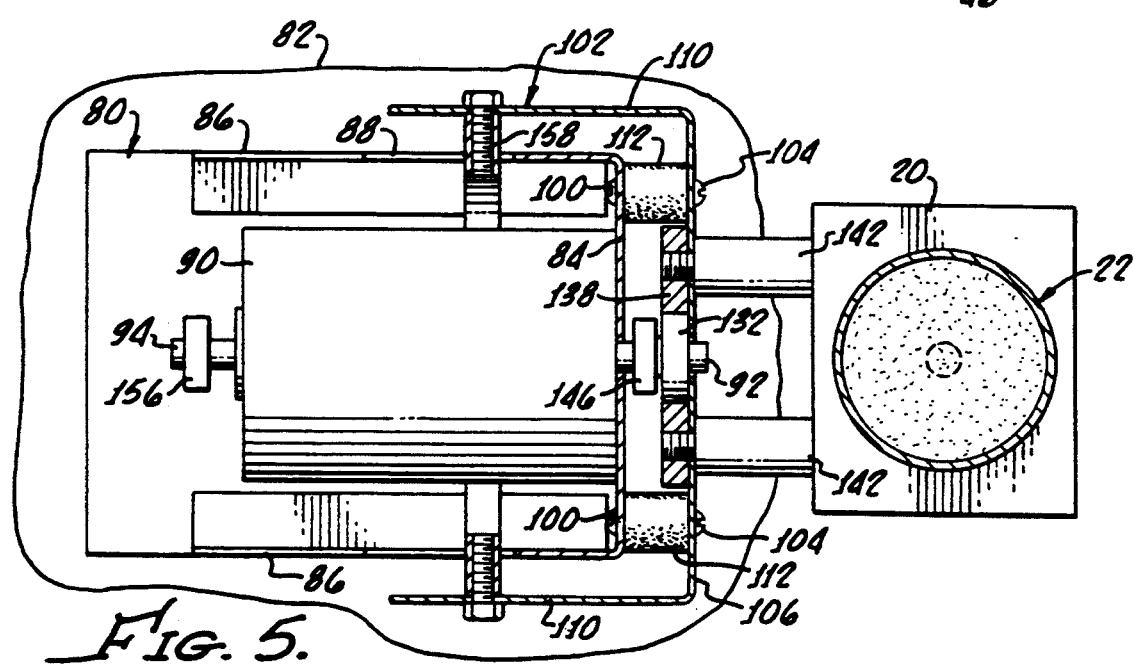

Also carried by the motor bracket 80 of the depicted exemplary embodiment of the invention are four horizontally extending equal-length elastomeric mounts 96, which at each end include a thread defining insert 98, viewing FIG. 5. The proximal ends of the mounts 96 are secured to the front plate portion 84 of motor bracket 80 by respective machine screws 100. At their distal ends, the mounts 96 carry a drive box member 102, which is similarly secured to the mounts by respective machine screws 104. Drive box 102 includes a vertical front wall portion 106, which is substantially parallel with front plate portion 84 of motor bracket 80, and a top wall portion 108 spanning between a pair of side wall portions 110. Those ordinarily skilled in the pertinent arts will recognize that the drive box 102 may be suspended by equivalent devices other than the elastomeric mounts 96. For example, a flexible resilient mounting device allowing its opposite ends to move in parallel planes relative to one another may be substituted for the elastomeric mounts 96. One version of such a device takes the form of an elongate open coil spring with provision at each of its opposite ends for securing to supporting and supported structure. This and other such flexible mounting devices can be substituted for the elastomeric mounts 96. Also, other numbers of such mounts may be used to support the drive box 102. For example, three or a larger number of such flexible mounting devices may support the drive box 102 from bracket 80. Still alternatively, a single annular flexible mounting structure could be used to circumscribe the motor shaft portion 92 and extend between the bracket 80 and drive box 102.

Because the mounts 96 are flexible and elastomeric, the drive box 102 has a limited freedom of movement relative to the motor mount 80. In order to constrain the movement of the drive box 102 in a defined vertical plane, the depicted exemplary embodiment of the invention includes four sleeve-like bushings 112 which are received about the mounts 96. The bushings 112 define a bore 114 having a diameter somewhat larger than the outside diameter of the mounts 96 so that the mounts and bushings do not interfere with one another, referring particularly to FIGS. 5 and G. Each bushing 112 defines opposite end surfaces 11G, 118, which slidably engage the motor mount 80 and drive box 102, respectively. Because the bushings 112 are substantially the same length as the mounts 96, front wall 106 of the drive box 102 is constrained to move in a plane parallel with the front plate portion 84 of the motor mount bracket 80, which is a vertical plane. Moreover, the drive box 102 can slidably move both vertically and horizontally, as well as rotate in the vertical plane defined by the adjacent end surfaces 118 of the bushings 112.

To orbitally couple the motor 90 with drive box 102, the shaft 92 carries an eccentric drive and counterbalance assembly 120, best seen in FIGS. 6 and 7. The drive assembly 120 includes a unitary eccentric shaft and counter weight member 122, which defines a through bore 124 receiving the shaft 92. A set screw 126 threadably received in a bore 128 intersecting with the bore 124 engages the shaft 92 to drivingly couple the member to shaft 92. Outwardly of the shaft 92, and away from the motor 90, the member 122 defines an eccentric stem 130. Carried on the stem 130 is a ball bearing 132, the outer race 134 of which is received into a bore 136 of a drive plate 138, viewing FIG. 6. The drive plate 138 is secured to the front wall portion 106 of the drive box 102 by four fasteners 140. Two of the fasteners 140 are elongate, and receive thereon a pair of sleeve members 142 which at their outer end carry the sample cup clamp 20. Viewing FIG. 4, it is seen that the sleeves 142 extend outwardly of the cover 78 via an aperture 144 therein into the sample chamber 18.

FIGS. 6 and 7 also show that the eccentric drive and counterbalance assembly includes as an integral part of the member 122, a counterbalance arm portion 146. This arm portion 146 is angularly disposed relative to the eccentric stem at a position in line with the center of eccentricity of the stem 130. As is depicted in FIG. 7, rotation of the motor shaft 92 (arrow 148) rotates the eccentric stem 130 and results in orbital relative displacement of the drive plate 138 and drive box 102, as is depicted by double ended arrow 150. While this orbital displacement appears like a reciprocation when viewed in a plane like the view of FIG. 7, it will be understood that the displacement oft he drive box 102 relative to the motor end shaft portion 92 is orbital. For this reason, in FIG. 6 a double ended arrow 150 appears in association with the sample cup holder 20 as a reminder of the orbital nature and orientation of the motion imposed on this sample cup by the vibratory drive 76. This orbital displacement of the drive plate and box 138 and 102 is a result of a displacing force which originates with the eccentric stem 130 and is applied at drive plate 138. The inertial reaction force of this displacing force is effective on the shaft end portion 92, and is represented by arrow 152. To counter the force 152, the counterbalance arm portion supplies a centrifugal force indicated by arrow 154. The force represented by arrow 154 is in the opposite direction and substantially matches in magnitude the force 152. However, because the two forces 152 and 154 are laterally offset relative to one another by a small amount, a small rocking couple or moment would be effective on the motor 90 via shaft 92. To counterbalance this small rocking couple and provide an even quieter vibratory drive, the end shaft 94 drivingly carries a small counterbalance arm 156. This counterbalance arm 156 is aligned 180° out of phase with both the center of the eccentricity of the stem 130 and the arm 146.

Figure 4:
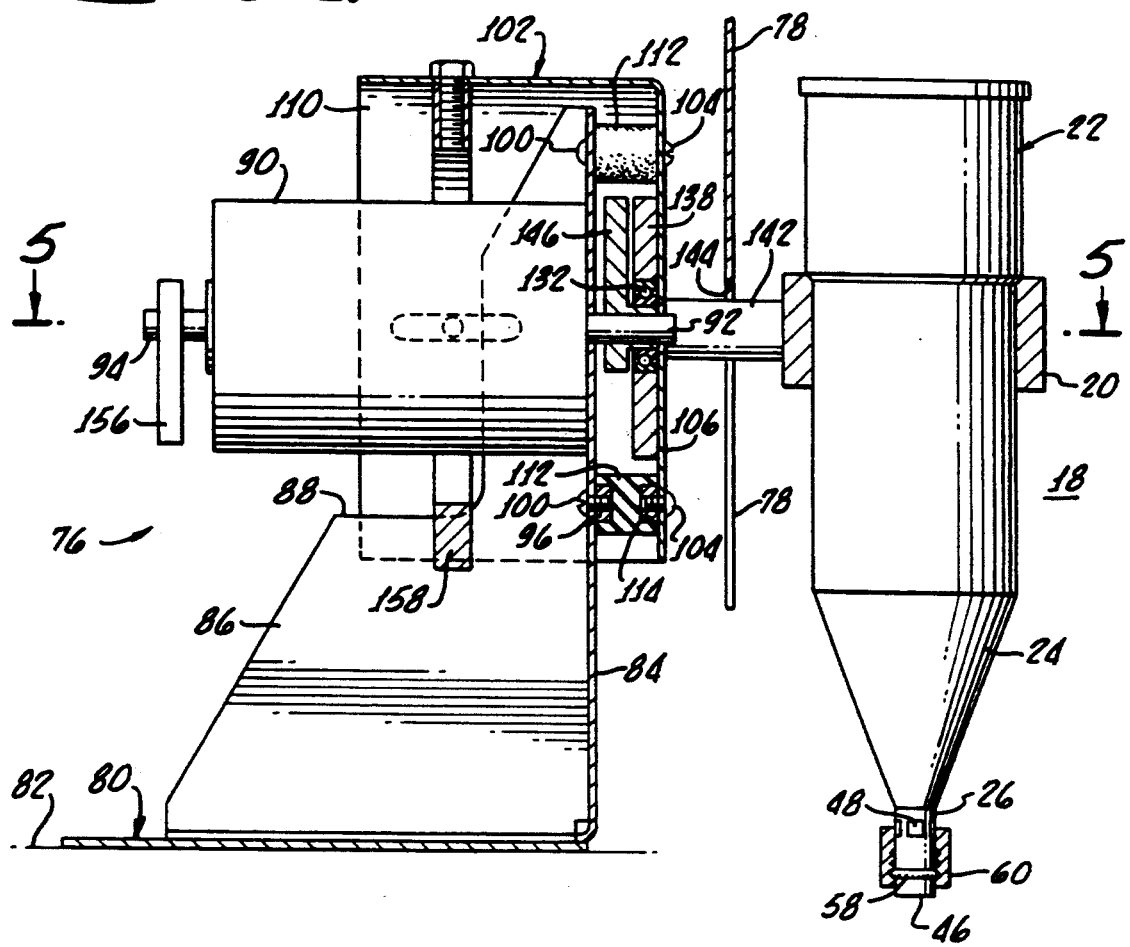

Finally, in order to both statically and dynamically balance the drive box 102, and components carried thereby (including the sample cup clamp 20 and sample cup 22) at the plane of the front wall 106, as well as to inhibit rotation of the drive box in the vertical plane, the latter carries an annular counterbalance member 158 circumscribing the motor 90, as is seen in FIGS. 4–6. In other words the weight of the annular member 158 is chosen in view of its distance from the vertical plane at front wall 106 to provide static balance, while mass moments are also thus balanced at this plane with respect to the horizontal and vertical accelerations of the orbital movements effected in the plane. As a result, drive box 102 (and components carried thereby) does not tend to rock in a vertical or horizontal plane parallel to the motor shaft 92,94. Also, the annular counter balance member 158 provides a high polar moment of inertia about the axis of motor shaft 92,94 resisting rotation of the drive box in the vertical plane at the front wall 106. Consequently, any tendency of the drive box 102 to rock in this vertical plane, which would also rock the sample cup 22 and the spout 26 thereof in conduit 30, is resisted by the high rotational inertia of the annular counterbalance member 158.

In operation of a particle dispenser according to the present invention, the particulates are introduced into the chamber 40 of the sample cup 22 after the collar 60 has been placed in a selected position in view of the repose angle of the particulated. With the sample cup in the cup clamp 20, and the air flow system of the particle analyzer 10 in operation, the drive motor 90 is operated at a chosen speed in view of the feed characteristics of the particulates. The vibratory driver 76 orbitally oscillates the sample cup and particulates in a vertical plane parallel with the front wall 106 of the drive box 102, substantially without rocking in this, or other planes. The vertical orbital motion of the sample cup toilet he particulates to maintain homogeneity of the bulk sample. Also this orbital motion dislodges particles from their repose on the ledge surface 66 so that they tumble over edge 70 of collar member go into the conveying air stream 74. The Applicants have determined by testing of a dispenser according to the invention that a monotonic relationship exists between the speed of operation of motor 90 and the rate at which particles are dispersed from the sample cup 22. This feature, in addition to the control of particle flow rate made possible with movement of the collar 60, allows an easy, predictable and repeatable control of the drizzling of particles to the analyzer 10. Also, after use of the sample cup 22, the collar 60 simply pulls off the spout portion 26 to permit easy and quick cleaning of the sample cup. When the vibratory driver 76 is used with a conventional sieve screen type of sample cup, the sample roiling also helps prevent sample classification, while the vertical accelerations of the orbital motion provide a driving force over gravity to assist the particulates through the sieve screen.

In view of the above, it should be clearly understood that the orbital driver 76 of the present invention may be used with a conventional sieve screen type of sample cup. For example, the sample cup seen in FIG. 4 should be considered alternatively to be either a conventional sieve screen type, or the present inventive "window ledge", type of sample cup. The advantages deriving in particle analysis from dispersing particles from a bulk sample by use of a vertical orbital oscillatory drive of the sample cup are so significant and clear cut that no inference should be made requiring a particular type of sample cup. Significant advantages are to be had even with the conventional sieve screen sample cup.

To recap the structural and functional advantages provided by the present invention, the orbital oscillatory motion in a vertical plane, and substantially without angular rocking, which is imposed upon a sample cup by the present vibratory driver tends to roll the entire bulk sample in the sample cup so that homogeneity of the sample is maintained. Also, the vertical aspect of the orbital motion provides an acceleration in addition to gravity to assist the particles through the sieve screen when such a sample cup is used with the vibratory driver. The rate of orbiting may by increased to the level desired for urging the particles through the sieve.

On the other hand, the vertical orbital motion of the present vibratory driver seems to prevent the undesirable packing of the sample which sometimes results from the purely vertical shaking or reciprocation discussed in connection with conventional particulate dispensers. The present vibratory driver is also inertially balanced to avoid angular rocking of the sample cup and to maintain the sample cup in a vertical orientation during its orbital motion. Because the intake to a particle analyzer is generally not much bigger than the outlet of the sample cup, avoidance of angular rocking is desirable both to avoid having particles flung outside of the intake, and to avoid collision of the sample cup with the analyzer intake. Thus, lose of particulates outside the analyzer intake is avoided.

While the above-described vibratory sample cup driver is advantageously useable with conventional sieve screen sample cups, the above-described "window ledge" type of sample cup results in reduced classification of the sample by size, a resulting increase in uniformity of feeding of the bulk sample to a particle analyzer, and an important monotonic relationship between oscillation rate and sample feed rate. That is, an increase or decrease in the rate of vibration applied to the sample cup results in a respective increase or decrease in the rate of particle drizzle to the test cell. While the monotonic relationship may not necessarily be linear, at no time should the vibration rate and particle feed rate display an inverse relationship. A technician using the combination of the "window ledge" sample cup with the vertical orbital vibratory cup driver provided by the present invention will be able to much better control the rate and consistency of drizzling of a sample to the test cell of a particle analyzer. Thus, the accuracy and repeatability of particle size distribution tests conducted with the invention is considerably improved over the prior technology.

Finally, the vibratory driver provided by the present invention is very low in both audible and structural noise. As a result, the vibratory drive and sample cup may be stacked on the particle analyzer above the analysis cell thereof with a resulting vast improvement in particle flow for the analyzer, and decrease in space needed for the apparatus.

While the present invention has been disclosed and depicted, and is defined by reference to a single preferred embodiment of the invention, such reference does not imply a limitation on the invention, and no such limitation is to be inferred. The invention is intended to be limited only by the spirit and scope of the appended claims, which also provide a definition of the invention.

What is claimed

1. Apparatus for dispensing particulates comprising:
    sample cup means for defining a sample chamber into which a bulk sample of said particulates is receivable;
    said sample cup means also defining at least one window having an upper and a lower edge and opening outwardly of the sample cup chamber;

means defining a ledge extending substantially horizontally outwardly of the window and ending at a drop-off edge; and means for selectively vertically moving and retaining said means defining a ledge intermediate the window edges so that particulates may repose on the ledge;

whereby, in the absence of vibration the particulates lay on the ledge with an angle of repose characteristic of the particulate bulk, and when vibration is applied to the apparatus, particulates drizzle over the drop-off edge of the ledge means.

2. The apparatus of claim 1 wherein said sample cup means also includes a funnel-like portion with a lower spout portion, said at least one window being defined at said lower spout portion.

3. The apparatus of claim 2 wherein said means defining a ledge includes a collar member carried upon and circumscribing said spout portion said collar member including an annular ledge surface circumscribing said spout portion.

4. The apparatus of claim 2 wherein said spout portion further includes a floor downwardly closing said sample chamber, said window opening outwardly of said sample chamber with said lower edge thereof adjacent the level of said floor.

5. The apparatus of claim 2 wherein said spout portion further defines a plurality of windows opening at the same level from said sample chamber.

6. Apparatus for dispensing particulates comprising:
sample cup means for defining a sample chamber into which a bulk sample of said particulates is receivable;

said sample cup means also defining at least one window having an upper and a lower edge and opening outwardly of the sample cup chamber;

means defining a ledge extending substantially horizontally outwardly of the window and ending at a drop-off edge;

means for selectively vertically moving and retaining said means defining a ledge intermediate the window edges so that particulates may repose on the ledge;

wherein said sample cup means also includes a funnel-like portion with a lower spout portion, said at least one window being defined at said lower spout portion; and wherein said means defining a ledge includes a collar member carried upon and circumscribing said spout portion, said collar member including an annular ledge surface circumscribing said spout portion;

wherein said means for selectively moving and retaining said means defining a ledge includes said spout portion defining a circumferential groove, said collar member also defining a circumferential groove confronting said groove of said spout portion, and a resilient retention member received in said confronting grooves for retaining said collar member, said resilient member yielding to allow manual movement of said collar member along said spout portion;

whereby, in the absence of vibration the particulates lay on the ledge with an angle of repose characteristic f the particulate bulk, and when vibration is applied to the apparatus particulates drizzle over the drop-off edge of the ledge means.

7. The apparatus of claim 6 wherein said resilient elastomeric retention member also sealingly engages said spout portion and said collar member to prevent loss of particulates from said chamber between said spout portion and said collar member.

8. The apparatus of claim 6 wherein said collar member further includes a plurality of grooves into which said resilient retention member is selectively receivable by movement of said collar member on said spout portion.

9. The apparatus of claim 6 wherein said spout portion terminates in an end spaced below said window, said spout portion circumferential groove and said resilient retention member therein being disposed below said window lower edge and above said spout end.

10. The apparatus of claim 9 further including said collar member groove being disposed below said collar member ledge surface.

* * * * *